United States Patent
Clancy

(10) Patent No.: US 9,289,231 B2
(45) Date of Patent: Mar. 22, 2016

(54) METHOD FOR ACCESS NEEDLE WITH PRE-LOADED WIRE GUIDE AND DEVICE

(75) Inventor: Michael S. Clancy, Limerick (IR)

(73) Assignee: Cook Medical Technologies LLC, Bloomington, IN (US)

( * ) Notice: Subject to any disclaimer, the term of this patent is extended or adjusted under 35 U.S.C. 154(b) by 1103 days.

(21) Appl. No.: 13/196,278

(22) Filed: Aug. 2, 2011

(65) Prior Publication Data

US 2013/0035639 A1 Feb. 7, 2013

(51) Int. Cl.
*A61B 17/34* (2006.01)
*A61B 19/00* (2006.01)
*A61M 25/06* (2006.01)

(52) U.S. Cl.
CPC ............ *A61B 17/34* (2013.01); *A61B 17/3421* (2013.01); *A61B 17/3478* (2013.01); *A61B 2019/5425* (2013.01); *A61M 25/065* (2013.01)

(58) Field of Classification Search
CPC ............... A61B 17/34; A61B 17/3421; A61B 17/3478; A61B 2019/5425; A61M 25/065
See application file for complete search history.

(56) References Cited

U.S. PATENT DOCUMENTS

| 7,025,746 B2* | 4/2006 | Tal ............................. 604/164.1 |
| 2010/0160731 A1 | 6/2010 | Giovannini et al. |
| 2010/0191267 A1* | 7/2010 | Fox ................ A61B 17/320016 606/185 |

FOREIGN PATENT DOCUMENTS

WO WO 2010/083467 A2 7/2010

OTHER PUBLICATIONS

Irvin F. Hawkins, Jr. et al., *Transjugular IntrahepaticPortosystemic Shunt Procedure Using The Angiodynamics*, ©2002-2009, Grupo Cardiva.

* cited by examiner

*Primary Examiner* — Theodore Stigell
(74) *Attorney, Agent, or Firm* — Brinks Gilson & Lione

(57) ABSTRACT

A medical device is provided, configured to access a target site within a patient body. The device may be provided as a kit including pre-assembled components. Embodiments of the device include an elongate flexible access needle including a needle lumen disposed through at least a longitudinal length of the needle; an elongate wire guide pre-loaded into at least a lengthwise portion of the needle lumen and extending to at least near a distal end of the needle end; and a needle sheath including a longitudinal sheath lumen through which the access needle is disposed; where the distal needle end comprises a piercing tip configured for penetrating tissue to access a target site. A method of use is provided where the needle may be withdrawn over the pre-loaded wire guide after it has been directed to a target site and the sheath as been advanced over the needle's distal end, in a manner freeing the wire guide for further guidance or direction, and for introduction of another device along the wire guide.

12 Claims, 1 Drawing Sheet

METHOD FOR ACCESS NEEDLE WITH PRE-LOADED WIRE GUIDE AND DEVICE

TECHNICAL FIELD

Embodiments described herein relate to a device and method for minimally invasive surgical access. More particularly embodiments herein relate to an access needle device and method therefor.

BACKGROUND

Minimally invasive diagnostic and therapeutic surgical techniques have become increasingly common in usage. However, with the increase in use and availability, the devices and techniques continue to become more and more sophisticated. For certain procedures, such as accessing a pancreatic pseudocyst or other target site in a patient body, it is possible to use an access needle device. One such device utilizes a blunt access cannula housing a bevel-tipped stylet. The cannula of existing systems is blunt, because a sharp bevel-tipped needle may strip or otherwise damage a wire guide that is moved over/through it, which is why the stylet is used to provide the piercing tip while providing a cannula through which a wire guide may be advanced—including out of and past its distal end. The cannula and stylet are directed to a target site (e.g., via an endoscope working channel), where the stylet tip is used to puncture through target tissue to allow penetration of the access cannula. Thereafter, the stylet must be removed to free up the lumen of the access cannula so that a wire guide may be directed through that lumen.

For accessing structures like a pancreatic pseudocyst, the cannula is typically at least 180 cm in length. Thus, retracting and removing the style, then directing the wire guide all the way back through the lumen can be a time-consuming procedure. Because the time of the patient, treatment personnel, and facilities are at a premium, it would be advantageous to provide a system and method that will offer greater efficiency without sacrificing the benefits of such a minimally invasive procedure to provide a wire guide accessing a target site.

BRIEF SUMMARY

In one aspect, embodiments may include an access needle device including an elongate flexible needle, preloaded wire guide, and overlying sheath, as well as methods for use of that device, which may be provided in kit form.

In one aspect, an embodiment may include a method for directing an elongate access needle with a preloaded wire guide in its lumen, and an overlying sheath, to a target site, then advancing the sheath and retracting the needle in a manner configured to avoid damage to the wire guide. The needle may be removed completely, as may the sheath, and another device may be directed along the wire guide which is left in place at the target site and/or which may be directed to another desired location.

DETAILED DESCRIPTION

Figure 1:
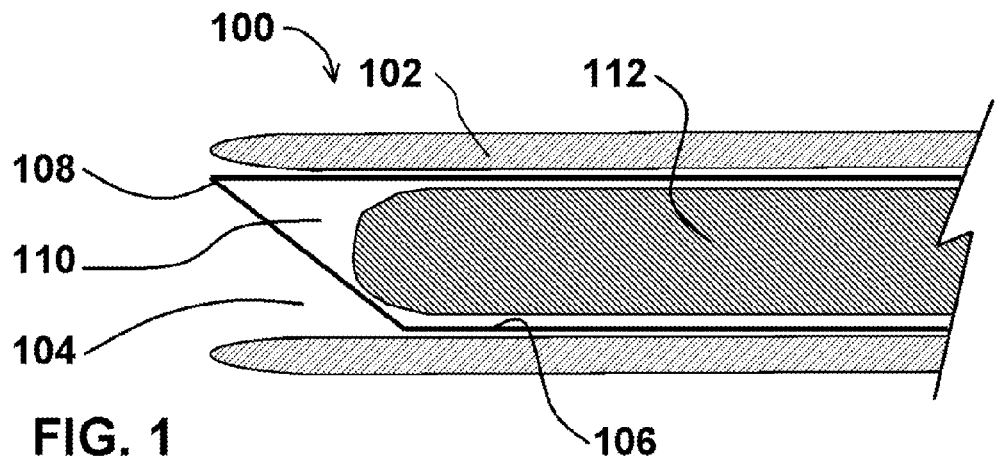
FIG. 1 shows a distal end of an access needle system including a preloaded wire guide and an outer sheath.
Figure 2:
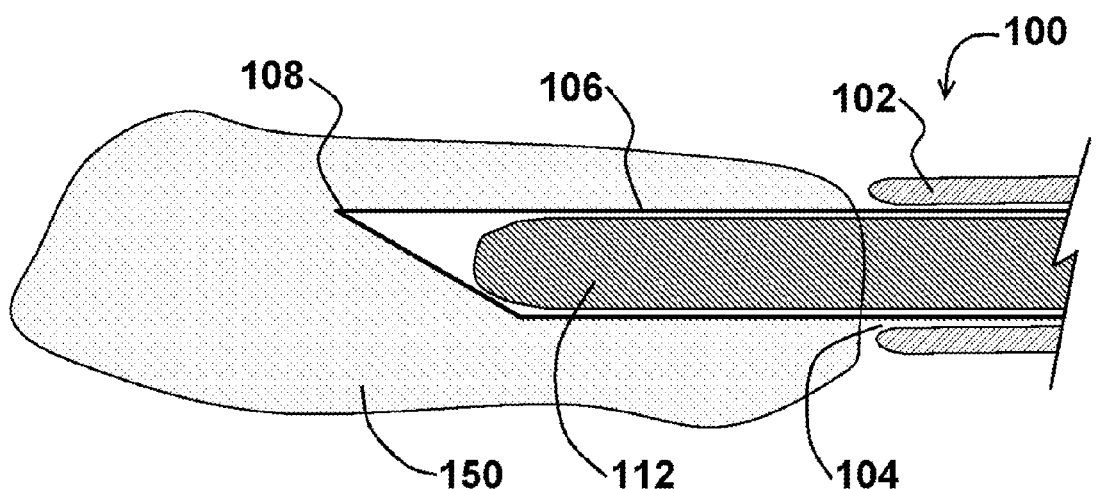
FIG. 2 shows the access needle of FIG. 1 penetrating a target mass.
Figure 3:
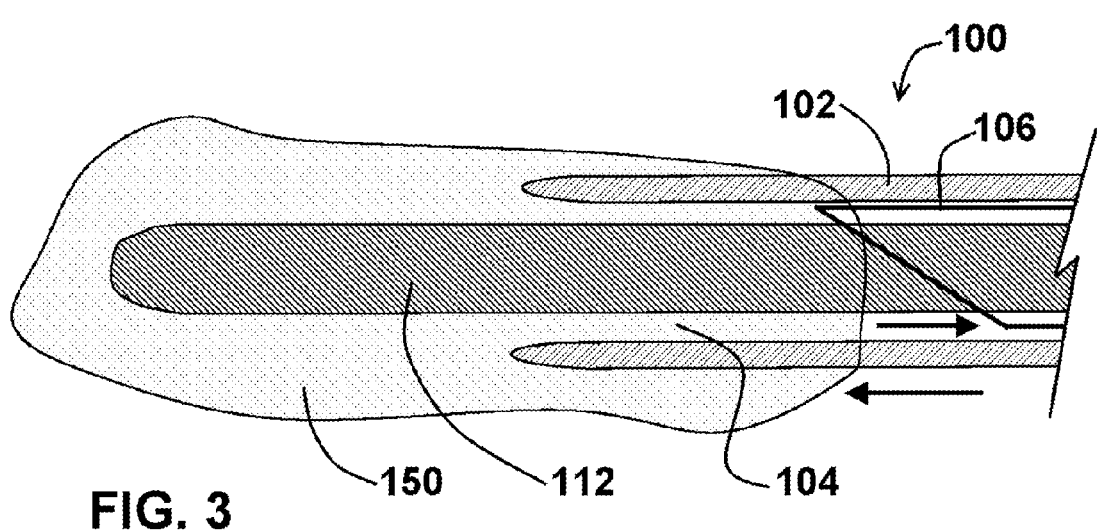
FIG. 3 shows the access needle of FIG. 1 being withdrawn proximally from the wire guide and sheath.

Embodiments are described with reference to the drawings in which like elements are generally referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments of the present invention, such as—for example—conventional fabrication and assembly. The terms "distal" and "proximal" are to be understood with their standard usages, referring to the direction away from and the direction toward the handle/user end of a tool or device, respectively (i.e., the term "distal" means the direction or portion of the device that is farthest from the physician or other person operating the tool or device and the term "proximal" means the portion of the device that is nearest to that physician or other person). In FIGS. 1-3 of this application, left corresponds with distal and right corresponds with proximal.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise.

A medical device 100 and method are described with reference to FIGS. 1-3. In certain preferred embodiments, the device shown in FIG. 1 may be provided as a pre-assembled kit. As shown in FIG. 1, an elongate flexible outer sheath 102 is provided. Polymer sheaths and other sheaths are known and used in the art for access needle systems and those of skill in the art will appreciate that a variety of sheath embodiments may be used with the presently described system within the scope of the claims. An elongate flexible access needle 106 is coaxially longitudinally disposed through at least a length of a sheath lumen 104 defined by the sheath 102. The needle 106 preferably will include a piercing tip, embodied here as a beveled tip 108. The needle 106 includes a needle lumen 110 extending through at least a longitudinal length thereof. A wire guide 112 is preloaded coaxially through at least a lengthwise portion of the needle lumen 110. The needle 106 is longitudinally slidable relative to both the wire guide 112 and the sheath 102, which are also each slidable relative to the needle 106.

Many different sizes of different embodiments of the presently described device may be used within the scope of the claims. As one example, the needle 106 may be configured as about a 19-gauge needle, and the wire guide 112 may be configured as about a 0.035" (0.89 mm) diameter wire guide. The needle 106 may include echogenic enhancements configured to enhance its visualization and navigation using ultrasound. Such enhancements may include one or more of surface dimpling, knurling, or other surface patterning on the external and/or lumenal surface(s) of the needle. The needle may be constructed of and/or may be constructed to include echogenic materials such as echogenic polymers, materials with echogenicity-enhancing inclusions, and/or any other materials now known, or yet to be developed, that will provide for ultrasound navigation.

A method of using the device 100 is described with reference to FIGS. 2-3. In FIG. 2, the needle device 100 has been provided and has been directed to a target site, which is embodied here—for the sake of illustrative example only—as a mass 150. The distal portion of the needle device 100 shown in FIGS. 1-3 may be directed thereto via the working channel of an endoscope (such as, for example, a gastrointestinal endoscope, duodenoscope, or other minimally invasive device configured for surgical access and/or visualization). The piercing tip 108 may be advanced penetratingly through tissue and/or into the mass 150 with the wire guide 112 disposed within, and immediately adjacent the distal end of, the needle lumen 110. The sheath 102 is shown as remaining outside the mass 150, although it may be advanced therein simultaneously with the needle 106.

As shown in FIG. 3, the sheath 102 may be advanced into the mass 150 to a position distal of the distal needle end 108. Then, the needle 106 may be proximally withdrawn and retracted some distance along at least a partial length of the wire guide 112, which may include complete withdrawal and removal from the wire guide 112. The relative coaxial positions of the wire guide 112, needle 106, and sheath 102 are configured to prevent the needle from stripping or otherwise damaging the wire guide 112. The sheath 102 may also be removed. The wire guide 112 may then be advanced, retracted, or otherwise directed to a desired location that may be, for example, in or near the target site mass 150. Another device (not shown) may be directed distally along the wire guide 112 to the target site 150 or to another desired location to which the wire guide 112 has been directed.

A kit including preassembled components as described above may be provided and be useful for implementing a variety of diagnostic and/or treatment procedures. For example, it may be advantageous to efficiently provide wire guide access to a pancreatic pseudocyst or a site in a patient's abdomen accessible via the biliary tree and/or NOTES (natural orifice translumenal endoscopic surgery) or other minimally invasive procedure. It should be appreciated that the pre-assembled nature of the wire guide, needle, and sheath will offer efficiencies for procedure time, manufacturing expense, and ease of use.

Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. Although specific terms are employed herein, they are used in a generic and descriptive sense only and not for purposes of limitation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment of the invention.

I claim:

1. A method for accessing a target tissue in a patient body, the method comprising:
   providing
      an access needle including a needle lumen disposed through at least a longitudinal length of the needle,
      a wire guide pre-loaded coaxially into at least a lengthwise portion of the needle lumen, and
      a sheath including a sheath lumen, wherein at least a distal length of the access needle is disposed through the sheath lumen;
   directing the wire guide and a distal needle end of the access needle simultaneously through a working channel of an endoscope to penetrate the target tissue,
      wherein during a portion of the directing step, a distal needle end tip of the access needle is disposed within the sheath lumen,
      wherein during a portion of the directing step, the distal needle end tip of the access needle is disposed outside and distal of the sheath lumen, and
      wherein the directing step is executed after the providing step;
   advancing the sheath distally along the access needle until a distal sheath end penetrates the target tissue,
      wherein during a portion of the advancing step, the distal sheath end is distal of the distal needle end tip, and
      wherein the advancing step is executed after the directing step; and
   retracting the needle along at least a partial length of the wire guide,
      wherein the retracting step is executed after the directing step.

2. The method of claim 1, wherein the retracting step is executed after the advancing step.

3. The method of claim 2, wherein the step of retracting the needle along at least a partial length of the wire guide comprises:
   removing the needle and the sheath from the wire guide; and
   further comprising a step of advancing a device distally along the wire guide.

4. The method of claim 1, wherein the step of retracting the needle along at least a partial length of the wire guide comprises:
   removing the needle and the sheath from the wire guide; and
   further comprising a step of advancing a device distally along the wire guide.

5. The method of claim 1, further comprising a step of further directing the wire guide to a desired location.

6. The method of claim 1, wherein the step of retracting the needle along at least a partial length of the wire guide comprises:
   removing the needle from the wire guide; and
   further comprising a step of advancing a device distally along the wire guide.

7. The method of claim 1, wherein the distal needle end of the access needle is configured as a piercing tip.

8. The method of claim 7, further comprising a step of further directing the wire guide to a desired location.

9. The method of claim 8, wherein the step of retracting the needle along at least a partial length of the wire guide comprises:
   removing the needle from the wire guide; and
   further comprising a step of advancing a device distally along the wire guide.

10. A method of medical access, said method comprising steps of:
   providing a kit including pre-assembled components, the kit comprising,
      an elongate flexible access needle including a needle lumen disposed through at least a longitudinal length of the needle;
      an elongate wire guide pre-loaded coaxially into at least a lengthwise portion of the needle lumen and extending to at least near a distal end of the needle end; and
      a needle sheath including a longitudinal sheath lumen through which a distal length of the access needle is disposed;

wherein the distal needle end comprises a piercing tip configured for penetrating tissue to access a target site;

directing the wire guide and a distal needle end of the access needle simultaneously through a working channel of an endoscope to penetrate a target tissue, wherein during a portion of the directing step, a distal needle end tip of the access needle is disposed within the sheath lumen, wherein during a portion of the directing step, the distal needle end tip of the access needle is disposed outside and distal of the sheath lumen, and wherein the directing step is executed after the providing step;

advancing the sheath distally past the distal needle end until a distal sheath end penetrates the target tissue, wherein during a portion of the advancing step, the distal sheath end is distal of the distal needle end tip, and wherein the advancing step is executed after the directing step; and retracting the needle proximally along the wire guide, wherein the retracing step is executed after the directing step.

11. The method of claim 10, wherein the step of retracting the needle further comprises removing the needle from the wire guide and directing another device distally along the wire guide.

12. The method of claim 10, further comprising a step of directing a distal wire guide end to a desired location.

\* \* \* \* \*